United States Patent
Peters et al.

(10) Patent No.: US 7,332,507 B2
(45) Date of Patent: Feb. 19, 2008

(54) 3-SUBSTITUTED QUINUCLIDINES AND THEIR USE

(75) Inventors: Dan Peters, Ballerup (DK); Gunnar M. Olsen, Ballerup (DK); Elsebet Østergaard Nielsen, Ballerup (DK); Philip K. Ahring, Ballerup (DK); Tino Dyhring Jørgensen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 491 days.

(21) Appl. No.: 10/512,570

(22) PCT Filed: May 27, 2003

(86) PCT No.: PCT/DK03/00354

§ 371 (c)(1),
(2), (4) Date: Oct. 26, 2004

(87) PCT Pub. No.: WO03/101987

PCT Pub. Date: Dec. 11, 2003

(65) Prior Publication Data

US 2005/0176756 A1 Aug. 11, 2005

(30) Foreign Application Priority Data

May 30, 2002 (DK) ................................ 2002 00834

(51) Int. Cl.
- *A01N 43/90* (2006.01)
- *A61K 31/44* (2006.01)
- *C07D 453/02* (2006.01)

(52) U.S. Cl. ...................................... 514/305; 546/133
(58) Field of Classification Search ................ 546/133; 514/305

See application file for complete search history.

(56) References Cited

U.S. PATENT DOCUMENTS 5,227,386 A * 7/1993 Bottcher et al. ............ 514/305
7,087,750 B2 * 8/2006 Caldirola et al. ........... 540/575
2004/0142935 A1 * 7/2004 Schiemann et al. ......... 514/250
2005/0101649 A1 * 5/2005 Schiemann et al. ......... 514/375

FOREIGN PATENT DOCUMENTS

| WO | WO-93/23395 A1 | 11/1993 |
| WO | WO-01/36417 A1 | 5/2001 |
| WO | 02/20521 * | 3/2002 |
| WO | WO-02/20521 A | 3/2002 |
| WO | WO-02-44176 A1 | 6/2002 |
| WO | WO-02/088143 A | 11/2002 |

OTHER PUBLICATIONS

Decker et al., Life Sciences, vol. 56, pp. 545-570.*
Geetha et al., Biochemistry, vol. 31, pp. 5488-5499.*
Coe et al., Tetrahedron Letters, vol. 37, pp. 6045-6048.*
Sobolov et al., Tetrahedron Letters, vol. 39, pp. 5685-5688.*
Mikhlina E E et al., Synthesis and pharmacological study of 2-(quinuclidyl)-substituted imidazolines and benzimidazoles, vol. 7, No. 12, 1973, pp. 23-26.
Nilsson et al., J. Med. Chem. 1995, 38, 473-487.
Nordvall et al., J. Med. Chem. 1996, 39, 3269-3277.
Johansson et al., J. Med. Chem. 1997, 40, 3804-3819.

* cited by examiner

*Primary Examiner*—Margaret D. Seamani
*Assistant Examiner*—Niloofar Rahmani
(74) *Attorney, Agent, or Firm*—Birch, Stewart, Kolasch & Birch, LLP

(57) ABSTRACT

This invention relates to novel 3-substituted quinuclidine derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

5 Claims, No Drawings

3-SUBSTITUTED QUINUCLIDINES AND THEIR USE

TECHNICAL FIELD

This invention relates to novel 3-substituted quinuclidine derivatives, which are found to be cholinergic ligands at the nicotinic acetylcholine receptors and modulators of the monoamine receptors and transporters.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

Nilsson et al. [Nilsson B M, Sundquist S, Johansson G, Nordvall G, Glas G, Nilvebrant L & Hacksell U; *J. Med. Chem.* 1995 38 473-487] describe the synthesis and muscarinic activity of certain 3-heteroaryl substituted quinuclidin-2-ene derivatives including 3-(2-benzofuranyl)quinuclidine-2-ene, 3-(3-benzofuranyl)quinuclidine-2-ene, 3-(2-benzothienyl)quinuclidine-2-ene, 3-(3-benzothienyl)quinuclidine-2-ene, 3-(2-benzoxazolyl)quinuclidine-2-ene, 3-(2-benzthiazolyl)quinuclidine-2-ene, 3-(2-benzofuranyl)quinuclidine and 3-(2,3-dihydrobenzofuran-2-yl)quinuclidine.

Nordvall et al. [Nordvall G, Sundquist S, Johansson G, Glas G, Nilvebrant L & Hacksell U; *J. Med. Chem.* 1996 39 3269-3277] describe the synthesis and muscarinic activity of certain quinuclidine-2-ene derivatives including 3-(2-benzofuranyl)-quinuclidine-2-ene and 3-(2-furo[3,2-b]pyridinyl)quinudidine-2-ene.

Johansson et al. [Johansson G, Sundquist S, Nordvall G, Nilsson B M, Brisander M, Nilvebrant L & Hacksell U; *J. Med. Chem.* 1997 40 3804-3819] describe the synthesis of certain quinuclidine-2-ene derivatives useful as muscarinic antagonists.

WO 93/23395 (Kabi Pharmacia) describes heteroaromatic quinuclidinenes and their activity on muscarinic acetylcholine receptors.

However, the 3-substituted heteroaromatic quinuclidine derivatives of the present invention have never been disclosed.

SUMMARY OF THE INVENTION

The present invention is devoted to the provision of new quinuclidine derivatives that are modulators of the nicotinic and/or of the monoamine receptors, and which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

Accordingly, in its first aspect the invention provides 3-substituted quinuclidine derivatives represented by Formula I:

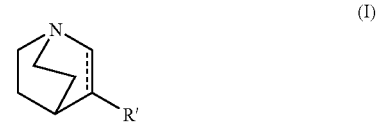

wherein

- - - - represents an optional double bond; and

R' represents an indolyl group, a benzimidazolyl group or a benzotriazolyl group, which heteroaryl group is optionally substituted one or more times with alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkenoxy, alkoxyalkenyl, alkynyl, alkoxyalkynyl, alkynoxy, alkylthio, alkylseleno, methylenedioxy, trifluoromethanesulfonyloxy, halo, haloalkyl, hydroxy, haloalkoxy, cyano, amino, nitro, oxime, alkyloxime, acyloxime, aryl, heteroaryl, and/or a group of the formula —(CO)$R^4$, —COO$R^4$, —O(CO)$R^4$, —CON$R^3R^4$, —NH—CO$_2R^3$, —NHCO—$R^3$ or —OCO—N$R^3R^4$; in which formulas $R^3$ and $R^4$ independently of one another represents hydrogen or alkyl;

any of its enantiomers or any mixture of enantiomers, or a pharmaceutically acceptable salt thereof, or an aza-onium-salt thereof.

In a second aspect the invention provides pharmaceutical compositions comprising a therapeutically effective amount of a 3-substituted quinuclidine derivative of the invention, or a pharmaceutically acceptable addition salt thereof, together with at least one pharmaceutically acceptable carrier or diluent.

Viewed from another aspect the invention relates to the use of a 3-substituted quinuclidine derivative of the invention for the treatment, prevention or alleviation of a disease or a disorder or a condition that is responsive to the action of a nicotinic acetylcholine receptor modulator.

In yet another aspect the invention provides a method of the treatment or alleviation of a disease or disorder of a living animal body, including a human, which disease or disorder is responsive to the action of a nicotinic acetylcholine receptor modulator, which method comprises the step of administering to such a living animal body, including a human, in need thereof a therapeutically effective amount of the 3-substituted quinuclidine derivative of the invention.

Other objects of the invention will be apparent to the person skilled in the art from the following detailed description and examples.

DETAILED DISCLOSURE OF THE INVENTION

3-Substituted Quinuclidine Derivatives

In its first aspect the invention provides novel 3-substituted quinuclidine derivative represented by Formula I:

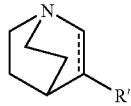

(I)

wherein

- - - - represents an optional double bond; and

R' represents an indolyl group, a benzimidazolyl group or a benzotriazolyl group, which heteroaryl group is optionally substituted one or more times with alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkenoxy, alkoxyalkenyl, alkynyl, alkoxyalkynyl, alkynoxy, alkylthio, alkylseleno, methylenedioxy, trifluoromethanesulfonyloxy, halo, haloalkyl, hydroxy, haloalkoxy, cyano, amino, nitro, oxime, alkyloxime, acyloxime, aryl, heteroaryl, and/or a group of the formula —(CO)R$^4$, —COOR$^4$, —O(CO)R$^4$, —CONR$^3$R$^4$, —NH—CO$_2$R$^3$, —NHCO—R$^3$ or —OCO—NR$^3$R$^4$; in which formulas R$^3$ and R$^4$ independently of one another represents hydrogen or alkyl;

any of its enantiomers or any mixture of enantiomers, or a pharmaceutically acceptable salt thereof, or an aza-onium-salt thereof.

In a 1$^{st}$ preferred embodiment, the 3-substituted quinuclidine derivative of the invention is a compound of Formula II:

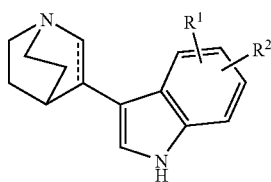

(II)

wherein

- - - - represents an optional double bond; and

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In a 2$^{nd}$ preferred embodiment, the 3-substituted quinudidine derivative of the invention is a compound of Formula III:

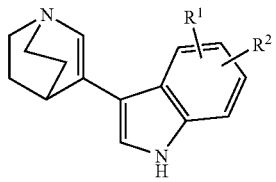

(III)

wherein

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—C$_{O2}$R$^2$, —NHCO—R$^2$ or —OCO—NR$^2$R$^3$; in which formulas R$^2$ and R$^3$ independently of each another represents hydrogen or alkyl.

In a more preferred embodiment the 3-substituted quinuclidine derivative of the invention is a compound of Formula II or III wherein R$^1$ and R$^2$, independently of one another, represent hydrogen, alkyl, cycloalkyl, cycloalkylalkyl, alkoxy, alkoxyalkyl, hydroxyalkoxy, halo, haloalkyl, hydroxy, haloalkoxy, cyano, amino, nitro or phenyl.

In an even more preferred embodiment the 3-substituted quinuclidine derivative of the invention is a compound of Formula II or III wherein R$^1$ and R$^2$, independently of one another, represent hydrogen, alkyl, alkoxy, halo, haloalkyl, hydroxy, cyano, amino, nitro or phenyl.

In a yet more preferred embodiment the 3-substituted quinuclidine derivative of the invention is a compound of Formula II or III wherein wherein one of R$^1$ and R$^2$ represents hydrogen, and the other of R$^1$ and R$^2$ represents alkyl, alkoxy, halo, haloalkyl, hydroxy, cyano, amino, nitro or phenyl.

In a most preferred embodiment the 3-substituted quinuclidine derivative of the invention is
3-(3-Indolyl)-quinuclidine-2-ene;
3-(5-Bromo-3-indolyl)-quinuclidine-2-ene;
3-(5-Methoxy-3-indolyl)-quinuclidine-2-ene;
3-(5-Phenyl-3-indolyl)-quinuclidine-2-ene;
any of its enantiomers or any mixture of enantiomers, or a pharmaceutically acceptable salt thereof, or an aza-onium-salt thereof.

In a 3$^{rd}$ preferred embodiment, the 3-substituted quinuclidine derivative of the invention is a compound of Formula IV:

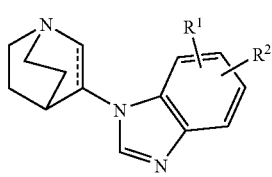

(IV)

wherein

- - - - represents an optional double bond; and

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In a 4$^{th}$ preferred embodiment, the 3-substituted quinuclidine derivative of the invention is a compound of Formula V:

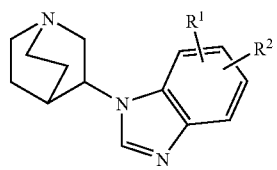

(V)

wherein

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In a more preferred embodiment, the 3-substituted quinuclidine derivative of the invention is a compound of Formula IV or V, wherein R$^1$ and R$^2$, independently of one another, represent hydrogen, alkyl, cycloalkyl, cycloalkylalkyl, alkoxy, alkoxyalkyl, hydroxyalkoxy, halo, haloalkyl, hydroxy, haloalkoxy, cyano, amino, nitro or phenyl.

In an even more preferred embodiment, the 3-substituted quinuclidine derivative of the invention is a compound of Formula IV or V, wherein R$^1$ and R$^2$, independently of one another, represent hydrogen, alkyl, alkoxy, halo, haloalkyl, hydroxy, cyano, amino, nitro or phenyl.

In a yet more preferred embodiment, the 3-substituted quinuclidine derivative of the invention is a compound of Formula IV or V, wherein one of R$^1$ and R$^2$ represents hydrogen, and the other of R$^1$ and R$^2$ represents alkyl, alkoxy, halo, haloalkyl, hydroxy, cyano, amino, nitro or phenyl.

In a most preferred embodiment, the 3-substituted quinuclidine derivative of the invention is (±)-3-(1-Benzimidazolyl)-quinuclidine;

(±)-3-(2-Trifluoromethyl-1-benzimidazolyl)-quinuclidine; or (±)-3-(5-Trifluoromethyl-1-benzimidazolyl)-quinuclidine;

any of its enantiomers or any mixture of enantiomers, or a pharmaceutically acceptable salt thereof, or an aza-onium-salt thereof.

In a 5$^{th}$ preferred embodiment, the 3-substituted quinuclidine derivative of the invention is a compound of Formula VI:

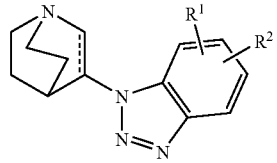

(VI)

wherein

- - - - represents an optional double bond; and

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In a 6$^{th}$ preferred embodiment, the 3-substituted quinudidine derivative of the invention is a compound of Formula VIII:

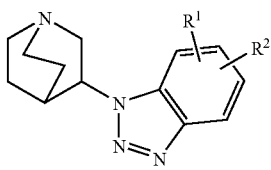

(VII)

wherein

R$^1$ and R$^2$, independently of one another, represent hydrogen, alkyl, cycloalkyl, cycloalkylalkyl, alkoxy, alkoxyalkyl, cycloalkoxy, alkoxycycloalkyl, cycloalkoxyalkoxy, hydroxyalkoxy, alkenyl, alkoxyalkenyl, alkynyl, alkoxyalkynyl, halo, haloalkyl, hydroxy, cyano, amino, nitro, phenyl, and/or a group of the formula —(CO)R$^3$, —COOR$^3$, —O(CO)R$^3$, —CONR$^2$R$^3$, —NH—CO$_2$R$^2$, —NHCO—R$^2$ or —OCO—NR$^2$R$^3$; in which formulas R$^2$ and R$^3$ independently of each another represents hydrogen or alkyl.

In a more preferred embodiment, the 3-substituted quinuclidine derivative of the invention is a compound of Formula VI or VII, wherein R$^1$ and R$^2$, independently of one another, represent hydrogen, alkyl, cycloalkyl, cycloalkylalkyl, alkoxy, alkoxyalkyl, hydroxyalkoxy, halo, haloalkyl, hydroxy, haloalkoxy, cyano, amino, nitro or phenyl.

In an even more preferred embodiment, the 3-substituted quinuclidine derivative of the invention is a compound of Formula VI or VII, wherein R$^1$ and R$^2$, independently of one another, represent hydrogen, alkyl, alkoxy, halo, haloalkyl, hydroxy, cyano, amino, nitro or phenyl.

In a yet more preferred embodiment, the 3-substituted quinuclidine derivative of the invention is a compound of Formula VI or VII, wherein one of R$^1$ and R$^2$ represents hydrogen, and the other of R$^1$ and R$^2$ represents alkyl, alkoxy, halo, haloalkyl, hydroxy, cyano, amino, nitro or phenyl.

In a most preferred embodiment, the 3-substituted quinuclidine derivative of the invention (±)-3-(1-Benzotriazolyl)-quinuclidine;

any of its enantiomers or any mixture of enantiomers, or a pharmaceutically acceptable salt thereof, or an aza-onium-salt thereof.

Definition of Substituents

In the context of this invention halo represents fluorine, chlorine, bromine or iodine.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl (allyl); 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octdienyl, or 1,3,5,7-octtetraenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of rom two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above, an alkenoxy group designates an "alkenyl-O—" group, wherein alkenyl is as defined above, an alkynoxy group designates an "alkynyl-O—" group, wherein alkynyl is as defined above, an alkoxyalkyl group designates an "alkyl-O-alkyl" group, wherein alkyl is as defined above, an alkoxyalkenyl group designates an "alkyl-O-alkenyl" group, wherein alkyl and alkenyl are as defined above, an alkoxyalkynyl group designates an "alkyl-O-alkynyl" group, wherein alkyl and alkynyl are as defined above, a cycloalkoxy group designates a "cycloalkyl-O—" group, wherein cycloalkyl is as defined above, a alkoxycycloalkyl group designates a "alkyl-O-cycloalkyl-" group, wherein alkyl and cycloalkyl are as defined above, and a cycloalkoxyalkoxy group designates a "cycloalkyl-O-alkyl-O—" group, wherein alkyl and cycloalkyl are as defined above.

In the context of this invention an alkylthio group designates an "alkyl-S—" group (thioalkoxy), wherein alkyl is as defined above, an alkenylthio group designates an "alkenyl-S—" group, wherein alkenyl is as defined above, and an alkynylthio group designates an "alkynyl-S—" group, wherein alkynyl is as defined above.

In the context of this invention an alkylseleno group designates an "alkyl-Se—" group, wherein alkyl is as defined above, an alkenylseleno designates an "alkenyl-Se—" group, wherein alkenyl is as defined above, and an alkynylseleno group designates an "alkynyl-Se—" group, wherein alkynyl is as defined above.

In the context of this invention an alkyloxime group designates a "C=N—O-alkyl" group, wherein alkyl is as defined above, and an acyloxime group designates a "C=N—O—COOH" group or a "C=N—O—CO-alkyl" group, wherein alkyl is as defined above.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl. In a most preferred embodiment the aryl group of the invention is phenyl.

In the context of this invention a heteroaryl group designates a mono-, bi- or polycyclic aromatic compound, which holds one or more heteroatoms in its ring structure. Preferred heteroatoms include nitrogen (N), oxygen (O), and sulphur (S). Preferred heteroaryl groups of the invention include the mono- and bi-cyclic heteroaryl groups.

Preferred monocyclic heteroaryl groups of the invention include aromatic 5- and 6 membered heterocyclic monocyclic groups, including furanyl, in particular 2- or 3-furanyl; thienyl, in particular 2 or 3-thienyl; pyrrolyl (azolyl), in particular 1,2 or 3-pyrrolyl; oxazolyl, in particular oxazol-2,4 or 5-yl; thiazolyl, in particular thiazol-2,4 or 5-yl; imidazolyl, in particular 1,2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-, 1,2,4-, 1,2,5- or 1,3,4-oxadiazol-3,4 or 5-yl; triazolyl, in particular 1,2,3-, 1,2,4-, 2,1,3- or 4,1,2-triazolyl; thiadiazolyl, in particular thiadiazol-3,4 or 5-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; and triazinyl, in particular 1,2,3-, 1,2,4- or 1,3,5-triazinyl.

Preferred bicyclic heteroaryl groups of the invention include indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2,5 or 6-benzofuranyl; benzo[b]thienyl, in particular 2,5 or 6-benzothienyl; benzimidazolyl, in particular 2,5 or 6-benzimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; pteridinyl, in particular 2,6 or 7-pteridinyl; and indenyl, in particular 1,2,3,5 or 5-indenyl.

Pharmaceutically Acceptable Salts

The 3-substituted quinudidine derivatives of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts (aza-onium salts). Preferred aza-onium salts include the alkyl-onium salts, in particular the methyl- and ethyl-onium salts; the cycloalkyl-onium salts, in particular the cyclopropyl-onium salts; and the cycloalkylalkyl-onium salts, in particular the cyclopropyl-methyl-onium salts.

Steric Isomers

The 3-substituted quinuclidine derivatives of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The 3-substituted quinuclidine derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The 3-substituted quinuclidine derivatives of the present invention show useful biological properties. In particular they are found to be cholinergic ligands at the nicotinic acetylcholine receptors (nAChR), and/or modulators of the monoamine receptors, in particular the biogenic amine transporters such as the serotonin receptor (5-HTR), the dopamine receptor (DAR) and the norepinephrine receptor (NER), and of the biogenic amine transporters for serotonin (5-HT), dopamine (DA) and norepinephrine (NE). The compounds of the present invention may in particular be agonists, partial agonists, antagonists and allosteric modulators of the receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a preferred embodiment diseases, disorders, or conditions relating to the central nervous system for which the compounds of the invention are used are cognitive disorders, psychosis, schizophrenia and/or depression.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Neuroimaging

The 3-substituted quinuclidine derivatives of the invention may be useful as diagnostic tools or monitoring agents in various diagnostic methods, and in particular for in vivo receptor imaging (neuroimaging).

In another aspect of the invention a method for the non-invasive determination of the distribution of a tracer compound inside a whole, intact living animal or human body using a physical detection method is provided. According to this method a tracer compound is a compound of the invention, or any of its enantiomers or any mixture thereof, or a pharmaceutically acceptable salt thereof, in labelled or unlabelled form.

In a preferred embodiment the physical detection method is selected from PET, SPECT; MRS, MRI, CAT, or combinations thereof.

The compounds of the invention may be used in their labelled or unlabelled form. In the context of this invention "label" stands for the binding of a marker to the compound of interest that will allow easy quantitative detection of said compound.

The labelled compound of the invention preferably contains at least one radionuclide as a label. Positron emitting radionuclides are all candidates for usage. In the context of this invention the radionuclide is preferably selected from $^{11}C$, $^{18}F$, $^{15}O$, $^{13}N$, $^{123}I$, $^{125}I$, $^{131}I$, $^{3}H$ and $^{99m}Tc$.

An examples of commercially available labelling agents, which can be used in the preparation of the labelled compounds of the present invention is $[^{11}C]O_2$, $^{18}F$, and NaI with different isotopes of Iodine.

In particular $[C^{11}]O_2$ may be converted to a $[^{11}C]$-methylating agent, such as $[^{11}C]H_3I$ or $[^{11}C]$-methyl triflate.

The tracer compound can be selected in accordance with the detection method chosen.

In one preferred embodiment, the labelled or unlabelled compound of the invention can be detected by a suitable spectroscopic method, in particular UV spectroscopy and/or fluorescence spectroscopy.

In anther preferred embodiment, the compounds of the invention are labelled by incorporation of a isotope into the molecule, which may in particular be an isotope of the naturally occurring atoms including deuterium, tritium, $^{13}C$, $^{14}C$, $^{131}I$, $^{125}I$, $^{123}I$, and $^{18}F$, the isotope incorporation may be measured by conventional scintillation counting techniques.

In a third preferred embodiment, the physical method for detecting said tracer compound of the present invention is selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Before conducting the method of the present invention, a diagnostically effective amount of a labelled or unlabelled compound of the invention is administered to a living body, including a human.

The diagnostically effective amount of the labelled or unlabelled compound of the invention to be administered before conducting the in-vivo method for the present invention is within a range of from 0.1 ng to 100 mg per kg body weight, preferably within a range of from 1 ng to 10 mg per kg body weight.

Pharmaceutical Compositions

In another aspect the invention provides novel pharmaceutical compositions comprising a therapeutically effective amount of a 3-substituted quinuclidine derivatives of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 3-substituted quinuclidine derivatives of the invention, or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired herapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The compounds of the present invention are valuable nicotinic acetylcholine receptor modulators and therefore useful for the treatment of a range of ailments involving cholinergic dysfunction as well as a range of disorders responsive to the action of nicotinic acetylcholine receptor modulators as well as the serotonin receptor.

Therefore, in another aspect the invention relates to the a method of the treatment or alleviation of a disease, disorder or condition of a living animal body, including a human, which disease, disorder or condition is responsive to the action of a nicotinic acetylcholine receptor modulator, which method comprises the step of administering to such a living animal body, including a human, in need thereof a therapeutically effective amount of the chemical compound of the invention.

The preferred indications for the method of the invention are those stated above.

In the context of this invention the term "treating" covers treatment, prevention, prophylaxis or alleviation, and the term "disease" covers illnesses, diseases, disorders and conditions related to the disease in question.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

General: All reactions involving air sensitive reagents or intermediates were performed under nitrogen and in anhydrous solvents. Magnesium sulphate was used as drying agent in the workup-procedures and solvents were evaporated under reduced pressure.

(±)-3-[Amino-1-(2-aminophenyl)]-quinuclidine (Intermediate compound)

A mixture of (±)-3-[amino-1-(2-nitrophenyl)]-quinuclidine (2.99 g, 12.5 mmol), palladium on carbon (500 mg, 10%, 50% water) and ethanol (50 ml) was stirred under hydrogen for 3.5 hours. The crude mixture was filtered through celite and was evaporated. The title compound was compound was isolated as an oil in quantitative yield (2.81 g, 12.5 mmol).

(±)-3-[Amino-1-(2-nitrophenyl)]-quinuclidine (Intermediate compound)

A mixture of (±)-3-aminoquinuclidine dihydrochloride (3.0 g 15.1 mmol) 1-fluoro-2-nitrobenzene (1.6 ml, 15.1 mmol), cecium carbonate (9.84 g, 30.2 mmol) and dimethylsulfoxide (5.0 ml) was stirred at 100° C. for 2 hours. Aqueous sodium hydroxide (50 ml, 1 M) was added followed by extraction with dichloromethane (2×50 ml). The combined organic phases were purified by chromatography on silica gel with dichloromethane, methanol and conc. ammonia (89:10:1) gave the title compound as an oil. Yield 2.99 g (80%).

Method A (±)-3-(1-Benzimidazolyl)-quinuclidine fumaric acid salt (Compound A1)

A mixture of (±)-3-[amino-1-(2-aminophenyl)]-quinuclidine (2.81 g, 12.5 mmol), formic acid (10 ml) and formaldehyde (10 ml) was stirred at reflux for 1.5 hours. The mixture was evaporated. Aqueous sodium hydroxide (100 ml, 1 M) was added to the mixture followed by extraction with dichloromethane (3×50 ml). The combined organic phases were purified by chromatography on silica gel with dichloromethane, methanol and conc. ammonia (89:10:1) and gave the title compound. Yield 0.14 g (5%).

The corresponding salt was obtained by addition of a diethyl ether and methanol mixture (9:1) saturated with fumaric acid. Mp 180.0-181.1° C.

(±)-3-(2-Trifluoromethyl-1-benzimidazolyl)-quinuclidine fumaric acid salt (Compound A2)

Was prepared from (±)-3-[amino-1-(2-aminophenyl)]-quinuclidine by Method A, using trifluoroacetic anhydride (instead of the mixture of formaldehyde and formic acid). Mp 188.4-189.4° C.

(±)-3-(5-Trifluoromethyl-1-benzimidazolyl)-quinuclidine fumaric acid salt (Compound A3)

Was prepared from (±)-3-[amino-1-(5-trifluoromethyl-2-aminophenyl)]-quinuclidine by Method A. Mp 185.5-187.1° C.

Method B 3-(3-Indolyl)quinuclidine-2-ene fumaric acid salt (Compound B1)

A mixture of 3-quinuclidinone (2.0, 16.0 mmol), indole (1.87 g, 16.0 mmol), sodium methoxide (1.73 g, 32 mmol) and methanol (40 ml) was stirred at reflux for 70 hours. The mixture was evaporated. Aqueous sodium hydroxide (100 ml, 1 M) was added followed by extraction with dichloromethane (3×50 ml). The combined organic phases were purified by chromatography on silica gel with dichloromethane, methanol and conc. ammonia (89:10:1) gave the title compound as an oil. The corresponding salt was obtained by addition of a diethyl ether and methanol mixture (9:1) saturated with fumaric acid. Yield 0.61 g (11%). Mp 138.1-138.8° C.

3-(5-Bromo-3-indolyl)quinuclidine-2-ene fumaric acid salt (Compound B2)

Was prepared according to Method B. Mp 271-275° C.

3-(5-Methoxy-3-indolyl)-quinuclidine-2-ene fumaric acid salt (Compound B3)

Was prepared according to Method B. Mp 216-217° C.

3-(5-Phenyl-3-indolyl)-quinuclidine-2-ene fumaric acid salt (Compound B4)

A mixture of 3-(5-bromo-3-indolyl)-quinuclidine-2-ene (2.18 g, 7.19 mmol), phenylboronic acid (1.31 g, 10.8 mmol), potassium carbonate (2.99 g, 21.6 mmol), 1,3-propandiol (1.56 ml, 21.6 mmol), palladacycle (67 mg, 0.072 mmol), tri-t-butylphosphine (14.5 mg, 0.072 mmol), palladium acetate (16 mg, 0.072 mmol) and 1.4-dioxane was stirred at reflux for 15 hours. The mixture was evaporated. Aqueous sodium hydroxide (100 ml, 1 M) was added followed by extraction with dichloromethane (3×50 ml). The combined organic phases were purified by chromatography on silica gel with dichloromethane, methanol and conc. ammonia (89:10:1) gave the title compound. The corresponding salt was obtained by addition of a diethyl ether and methanol mixture (9:1) saturated with fumaric acid. Yield 2.09 g (70%). Decomp. 246° C.

(±)-3-(1-Benzotriazolyl)-quinuclidine fumaric acid salt (Compound B5)

A mixture of (±)-3-[amino-1-(2-aminophenyl)]-quinuclidine (6.27 g, 28.9 mmol), water (60 ml), acetic acid (20 ml), concentrated hydrochloric acid (1 ml) and sodium nitrite (2.19 g, 31.7 mmol) was stirred at 80° C. for 2 hours. The mixture was allowed to reach room temperature. Aqueous sodium hydroxide (100 ml, 1 M) was added followed by extraction with dichloromethane (3×50 ml). The combined organic phases were purified by chromatography on silica gel with dichloromethane, methanol and conc. ammonia (89:10:1) gave the title compound as an oil. The corresponding salt was obtained by addition of a diethyl ether and methanol mixture (9:1) saturated with fumaric acid. Yield 2.59 g (26%). Mp 188.4-189.4° C.

Example 2

In Vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional-liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound | $IC_{50}$ (μM) |
| A1 | 0.40 |

What is claimed is:

1. A 3-substituted quinuclidine derivative, represented by Formula V:

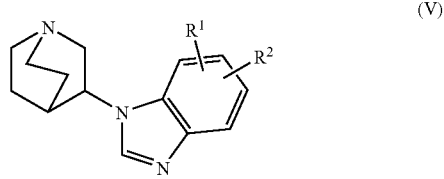

or by Formula VII:

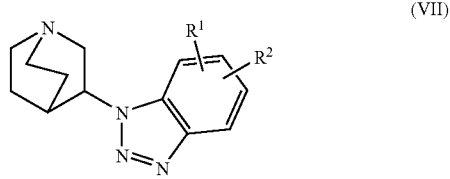

any of its enantiomers or any mixture of its enantiomers, or a pharmaceutically acceptable salt thereof, or an aza-onium-salt thereof, wherein $R^1$ and $R^2$, independently of each other, represent hydrogen, alkyl, cycloalkyl, cycloalkylalkyl, alkoxy, alkoxyalkyl, hydroxyalkoxy, halo, haloalkyl, hydroxy, haloalkoxy, cyano, amino, nitro or phenyl.

2. The quinuclidine derivative of claim 1, wherein $R^1$ and $R^2$, independently of each other, represent hydrogen, alkyl, alkoxy, halo, haloalkyl, hydroxy, cyano, amino, nitro or phenyl.

3. The quinuclidine derivative of claim 1, wherein one of $R^1$ and $R^2$ represents hydrogen, and the other of $R^1$ and $R^2$ represents alkyl, alkoxy, halo, haloalkyl, hydroxy, cyano, amino, nitro or phenyl.

4. The quinuclidine derivative of claim 1, which is
(±)-3-(1-Benzimidazolyl)-quinuclidine;
(±)-3-(2-Trifluoromethyl-1-benzimidazolyl)-quinuclidine;

(±)-3-(5-Trifluoromethyl-1-benzimidazolyl)-quinuclidine; or (±)-3-(1-Benzotriazolyl)-guinuclidine;

any of its enantiomers or any mixture of enantiomers, or a pharmaceutically acceptable salt thereof, or an aza-onmum-salt thereof.

5. A pharmaceutical composition comprising a 3-substituted quinuclidine derivative of claim 1, any of its enantiomers or any mixture of enantiomers, or a pharmaceutically acceptable salt thereof, together with at least one pharmaceutically acceptable carrier or diluent.

* * * * *